United States Patent
Voskuhl

(10) Patent No.: US 9,962,395 B2
(45) Date of Patent: May 8, 2018

(54) COMPOSITIONS AND METHODS FOR MAINTAINING COGNITIVE FUNCTION

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 15/515,058

(22) PCT Filed: Sep. 29, 2015

(86) PCT No.: PCT/US2015/052805
§ 371 (c)(1),
(2) Date: Mar. 28, 2017

(87) PCT Pub. No.: WO2016/053946
PCT Pub. Date: Apr. 7, 2016

(65) Prior Publication Data
US 2017/0232003 A1    Aug. 17, 2017

Related U.S. Application Data

(60) Provisional application No. 62/213,994, filed on Sep. 3, 2015, provisional application No. 62/056,944, filed on Sep. 29, 2014.

(51) Int. Cl.
*A61K 31/56* (2006.01)
*A61K 31/573* (2006.01)
*A61K 31/565* (2006.01)

(52) U.S. Cl.
CPC .......... *A61K 31/573* (2013.01); *A61K 31/565* (2013.01)

(58) Field of Classification Search
USPC ....................................................... 514/170
See application file for complete search history.

(56) References Cited

U.S. PATENT DOCUMENTS

| | | | |
|---|---|---|---|
| 4,826,831 A | 5/1989 | Plunkett et al. | |
| 5,108,995 A | 4/1992 | Casper | |
| 2005/0113350 A1* | 5/2005 | Duesterberg | A61K 31/56 514/170 |
| 2005/0239758 A1 | 10/2005 | Roby | |
| 2009/0005351 A1 | 1/2009 | Pickar et al. | |
| 2010/0168071 A1 | 7/2010 | Boissonneault | |

FOREIGN PATENT DOCUMENTS

| AU | 2004257772 A1 | 1/2005 |
|---|---|---|
| WO | WO-01070208 A2 | 9/2001 |
| WO | WO-2002/085374 | 10/2002 |
| WO | WO-2002/092102 A2 | 11/2002 |
| WO | WO-2002/092102 A3 | 11/2002 |
| WO | WO-2007/038435 A2 | 4/2007 |
| WO | WO-2007/038636 A2 | 4/2007 |
| WO | WO-2008/150547 A1 | 12/2008 |
| WO | WO-2010/050916 A1 | 5/2010 |

OTHER PUBLICATIONS

Anderer et al., Maturitas, 2005, 51(3): 254-69.*
Paula Alhola, The Journal of Obstetrics and Gynaecology Research, 2010, 36(4): 796-802.*
Gold et al., "Estrogen treatment in multiple sclerosis," J Neurol Sci, 286(1-2):99-103 (2009).
International Search Report of the International Searching Authority, dated Aug. 3, 2015, from related International Application No. PCT/US2015/027756.
International Search Report of the International Searching Authority, dated Aug. 5, 2015, from related International Application No. PCT/US2015/027752.
International Search Report of the International Searching Authority, dated Jan. 10, 2016, from related International Application No. PCT/US2015/047906.
International Search Report of the International Searching Authority, dated Jul. 11, 2016, from related International Application No. PCT/US2016/024754.
International Search Report of the International Searching Authority, dated Feb. 16, 2016, from related International Application No. PCT/US2015/056649.
International Search Report of the International Searching Authority, dated Jul. 21, 2016, from related International Application No. PCT/US2016/024751.
International Search Report of the International Searching Authority, dated Dec. 24, 2015, from related International Application No. PCT/US2015/052805.
Luchetti et al., "Gender Differences in Multiple Sclerosis: Induction of Estrogen Signaling in Male and Progesterone Signaling in Female Lesions," J Neuropathol Exp Neurol, 73(2): 123-135 (2014).
MacKenzie-Graham et al., "Estrogen treatment prevents gray matter atrophy in experimental autoimmune encephalomyelitis," J Neurosci Res, 90(7):1310-23 (2012).
Nicot, "Gender and sex hormones in multiple sclerosis pathology and therapy," Front Biosci (Landmark Ed), 14: 4477-4515 (2009).
Prempro and Premphase drug information, Food and Drug Administration, dated Jun. 5, 2003, Retrieved from the Internet. URL: http://www.fda.gov/ohrms/dockets/ac/03/briefing/3992B1_03_FDA-Prempro-Premphase.pdf.
Sicotte et al., "Treatment of Multiple Sclerosis with the Pregnancy Hormone Estriol," Ann Neurol, 52(4): 421-428 (2002).
Smith et al., "Impact of combined estradiol and norethindrone therapy on visuospatial working memory assessed by functional magnetic resonance imaging," J Clin Endocrinol Metab, 91(11):4476-81 (2006).
Speroff et al., "Postmenopausal hormone therapy," Gynecololgy and Obstetrics, Chapter 110, Mar. 8, 2011. URL: http://www.glowm.com/resources/glowm/cd/pages/v1/v1c110.html.
Anderson, "Adding estriol reduces ms relapse rate," Medscape Medical News, pp. 1-4 (2014). [https://www.medscape.com/viewarticle/824364].
Anonymous: "Estriol Treatment in Multiple Sclerosis (MS): Effect on Cognition," ClinicalTrials.gov archive, pp. 1-5 (2013). NCT01466114.

(Continued)

*Primary Examiner* — Rei Tsang Shiao
(74) *Attorney, Agent, or Firm* — Foley Hoag LLP

(57) ABSTRACT

Provided are methods for reducing the progression of cognitive decline in a post-menopausal woman using a continuous regimen of estrogen in combination with periodic administration of a progestogen.

20 Claims, 6 Drawing Sheets

(56) References Cited

OTHER PUBLICATIONS

Kipp et al., "Multiple sclerosis: neuroprotective alliance of estrogen-progesterone and gender," Front Neuroendocrin, 33(1):1-16 (2012).
Soldan et al., "Immune modulation in multiple sclerosis patients treated with the pregnancy hormone estriol," J Immunol, 171 (11):6267-6274 (2003).

* cited by examiner

COMPOSITIONS AND METHODS FOR MAINTAINING COGNITIVE FUNCTION

PRIORITY

This application is a § 371 national-stage application based on PCT Application PCT/US 15/052805, filed Sep. 29, 2015, which claims priority to U.S. Provisional Patent Application No. 62/056,944, filed Sep. 29, 2014, and U.S. Provisional Patent Application No. 62/213,994, filed Sep. 3, 2015, each of which is hereby incorporated by reference in its entirety.

BACKGROUND

Cognitive decline occurs in both men and women during andropause and menopause, respectively. Testosterone treatment is used to prevent cognitive decline in men with andropause, but no treatment is currently used or recommended to prevent cognitive decline in women with menopause. This is a major unmet clinical need for half of the population, and the need for therapy becomes more urgent as life expectancy increases. Testosterone is not preferred in women due to masculinizing side effects, and it has not been approved to preserve cognition in women. Hormone replacement for menopausal women generally involves treatment with estradiol, conjugated equine estrogens (CEE), or Premarin. These therapies, however, are associated with an increased risk of breast and uterine cancer as well as a cardiovascular risk, and thus they are either not recommended or are recommended only for short treatment durations to manage menopausal symptoms such as hot flushes and sweats. Thus, there remains a need for long-term treatments to reduce the progression of cognitive decline in women with menopause.

SUMMARY

An aspect of the invention is a method of reducing one or more symptoms of menopause in a female subject, comprising: administering to a female subject in need thereof, on a continuous basis throughout one or more (preferably at least two) consecutive treatment periods, a therapeutically effective amount of an estrogen; and administering to the subject, for only a portion of each treatment period, a therapeutically effective amount of a progestogen.

In certain embodiments, the estrogen is selected from estriol (E3), estradiol (E2), estrone (E1), pharmaceutically acceptable salts of any of the foregoing, and any combination thereof. In certain embodiments, the estrogen is estriol. In certain embodiments, the estrogen is administered orally in a dose equal or equivalent to about 2 mg of estriol daily. In certain embodiments, the estrogen is administered orally in a dose equal or equivalent to about 4 mg of estriol daily. In certain embodiments, the estrogen is administered orally in a dose equal or equivalent to about 6 mg of estriol daily. In certain embodiments, the estrogen is administered orally in a dose equal or equivalent to about 8 mg of estriol daily.

In certain embodiments, the progestogen is selected from chlormadinone acetate, cyproterone acetate, desogestrel, dienogest, 5α-dihydroprogesterone, drospirenone (Yasmin®), ethinodiol acetate, ethynodiol diacetate, etonogestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol, megestrol acetate (17α-acetoxy-6-dehydro-6-methylprogesterone), nestorone, nomegestrol acetate, norethindrone, norethindrone acetate (also known as norethisterone acetate), norethynodrel (Enovid®), norgestimate, norgestrel, progesterone, tanaproget, trimegestone, pharmaceutically acceptable salts of any of the foregoing, and any combination thereof. In certain embodiments, the progestogen is progesterone. In certain embodiments, the progestogen is norethindrone. In certain embodiments, the progestogen is administered orally in a dose equal or equivalent to about 700 µg of norethindrone daily.

An aspect of the invention is a method of reducing one or more symptoms of menopause in a female subject, comprising: administering orally to a female subject in need thereof, on a continuous basis for 84 consecutive days (12 weeks), 2 mg to 16 mg of estriol daily; and administering orally to the subject, for 14 consecutive days (2 weeks) of the 84 consecutive days (12 weeks), 0.7 mg of norethindrone daily. The method may comprise administering orally to the female subject about 2 mg, about 4 mg, about 6 mg, or about 8 mg of estriol daily.

In certain embodiments, the method further comprises administering to the subject a placebo in place of the norethindrone on each of the days the norethindrone is not administered to the subject.

In some embodiments, the one or more symptoms of menopause comprise impaired cognitive function and/or cognitive decline. In some embodiments, the one or more symptoms of menopause comprise impaired memory and/or memory loss. In some embodiments, the one or more symptoms of menopause comprise impaired learning and/or learning disability.

In certain embodiments, the method is a method for slowing, halting, or reversing cognitive decline in a post-menopausal female subject, comprising identifying a subject who has menopause and initiating treatment of the subject by a method as described herein. In certain embodiments, the method further comprises testing the severity of the subject's cognitive decline to determine a score representative of the state of the subject's cognitive decline after receiving the treatment for at least about six months, and, optionally, comparing the score to a score determined for the subject prior to or at about the time of initiating the treatment.

In certain embodiments, the method is a method for slowing, halting, or reversing memory loss in a post-menopausal female subject, comprising identifying a subject who has menopause and initiating treatment of the subject by a method as described herein. In certain embodiments, the method further comprises testing the severity of the subject's memory loss to determine a score representative of the state of the subject's memory after receiving the treatment for at least about six months, and, optionally, comparing the score to a score determined for the subject prior to or at about the time of initiating the treatment.

In certain embodiments, the method is a method for slowing, halting, or reversing learning disability in a post-menopausal female subject, comprising identifying a subject who has menopause and initiating treatment of the subject by a method as described herein. In certain embodiments, the method further comprises testing the severity of the subject's learning ability to determine a score representative of the state of the subject's learning ability after receiving the treatment for at least about six months, and, optionally, comparing the score to a score determined for the subject prior to or at about the time of initiating the treatment.

In other aspects, the invention relates to compounds for reducing one or more symptoms of menopause in a female subject according to any of the various methods disclosed herein, use of compounds in the manufacture of medicaments for carrying out any of the various methods disclosed herein, and kits comprising compounds together with instructions for administering the compounds according to any of the various methods disclosed herein. The one or more symptoms of menopause may comprise impaired cognitive function and/or cognitive decline. The one or more symptoms of menopause may comprise memory loss and/or learning disability.

Further, the present invention provides, inter alia, packaging designed to increase patient compliance with the treatment regime, in order to maximize the benefit and minimize the side effects of the treatment regime. In some aspects, the invention relates to a packaged pharmaceutical product, comprising a first region comprising a first series of doses of an estrogen, wherein each dose of the estrogen is associated with (e.g., adjacent or proximal to, or even co-located with) a dose of a progestogen; and a second region comprising a second series of doses of the estrogen that are not associated with doses of the progestogen. In such embodiments, the first region comprises both (i) a first series of doses of an estrogen and (ii) each dose of the progestogen with which the doses of estrogen are associated. In some embodiments, each dose of the estrogen in the second region is associated with a dose of placebo. In such embodiments, the second region comprises both (i) a second series of doses of an estrogen and (ii) each dose of the placebo with which the doses of estrogen are associated, such as in the manner that the doses of estrogen in the first series are associated with doses of the progestogen.

In certain embodiments, the invention relates to a method of using a packaged pharmaceutical product, comprising ingesting one dose of an estrogen and one dose of a progestogen daily from a first region of the product, and when the doses in the first region are exhausted, ingesting one dose of estrogen daily from a second region of the product. In some embodiments, when the doses in the first region are exhausted, the method comprises ingesting one dose of the placebo daily from the second region of the product with each dose of the estrogen from the second series with which the dose of the placebo is associated.

In certain embodiments, the invention relates to a method of using a packaged pharmaceutical product comprising ingesting one dose of an estrogen daily from a first region of the product, and when the doses from the first region are exhausted, ingesting one dose of the estrogen daily from a second region of the product.

DETAILED DESCRIPTION OF THE INVENTION

Figure 1:
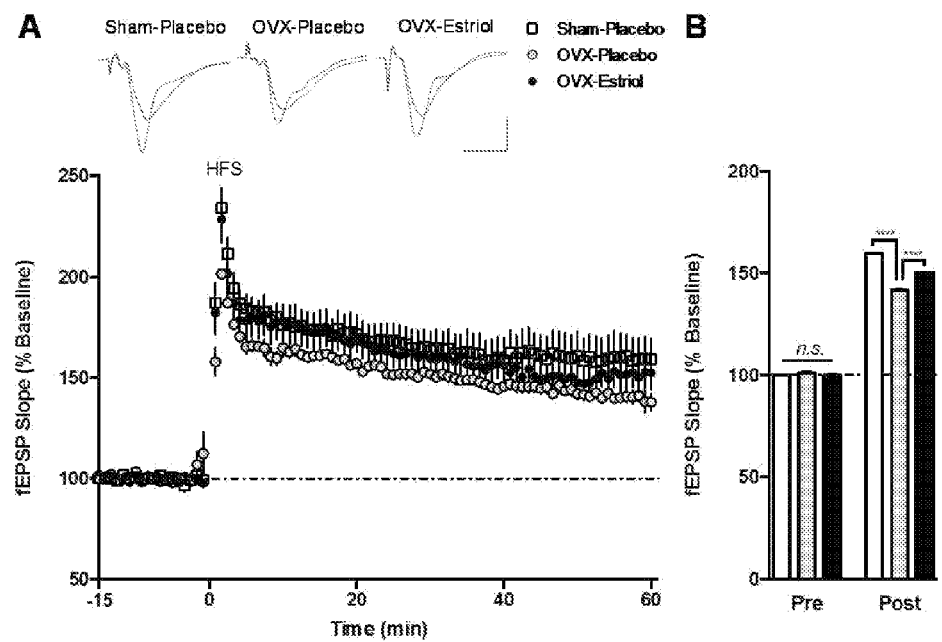
FIGS. 1A and 1B. Estriol partially recovers long term potentiation (LTP) in the hippocampal CA1 of ovariectomized (OVX) mice. (A) LTP induced by 2×100 Hz HFS in sham-placebo treated mice (open squares, n=4) is reduced in OVX-placebo treated mice (gray circles, n=4). Estriol-treated OVX mice show improved synaptic strength (black circles, n=4). Representative traces are superimposed average fEPSPs recorded at baseline and during final 15 minutes after HFS. Estriol (5 mg) or placebo was administered as subcutaneous pellets. Calibration: 2 mV, 5 ms. (B) Summary showing fEPSP slopes during baseline (Pre) and in final 15 minutes after HFS (Post). Estriol treatment gives significant improvement in LTP deficit from ovariectomy (Mean±SE post-HFS: sham-placebo, 159.6±0.2; OVX-placebo, 141.6±0.5; OVX-estriol, 150.4±0.4). *Statistics RM-ANOVA, Tukey's multiple comparison test*, ****$p \leq 0.0001$.

In certain aspects, the invention relates to methods of slowing, halting, or reversing cognitive decline or improving cognitive function in a menopausal female subject comprising administering a therapeutically effective amount of an estrogen to the subject. In some aspects, the invention relates to methods of slowing, halting, or reversing memory loss or improving memory in a menopausal female subject comprising administering a therapeutically effective amount of an estrogen to the subject. In certain aspects, the invention relates to methods of slowing, halting, reversing, or improving a learning disability in a menopausal female subject comprising administering a therapeutically effective amount of an estrogen to the subject.

Menopause

Natural menopause is the cessation of menses for 12 continuous months or more in the absence of a medical or surgical cause. Menopause may be induced medically, for example, by chemotherapy or radiation. Similarly, menopause may be induced surgically by the removal of the uterus (hysterectomy) with one or both ovaries conserved or bilateral removal of the ovaries (oophorectomy) with or without hysterectomy. Cessation of ovarian function may be difficult to assess in those who have only had the uterus removed or the uterus plus one ovary removed, as there may be a long gap between cessation of menses and cessation of ovarian function. Cessation of ovarian function is immediate, however, upon bilateral removal of ovaries (oophorectomy) with or without a hysterectomy. A woman's menopausal age is the age at last menses beyond which no menses has occurred for one year for natural menopause, or the date of surgery for surgical menopause. The average age of menopause in the United States is 51 years. Natural early menopause is defined as natural menopause between the ages of 40 and 45 years. Premature natural menopause is defined as natural menopause before the age of 40 years. A person is perimenopausal if the woman has not had a menses in 3 to 12 months. A woman is postmenopausal if either the woman has had no menses in the prior 12 months or has a loss of menses due a hysterectomy and/or bilateral oophorectomy (ovariectomy).

Hormone Replacement Therapy

No treatment is currently used or recommended to counter cognitive decline in menopausal women. Testosterone treatment is used to prevent cognitive decline in andropausal men, but testosterone is not desirable in women due to masculinizing side effects, and it has not been approved to preserve cognition in women. Hormone replacement for menopausal women generally involves treatment with estradiol, conjugated equine estrogens (CEE), or Premarin. These therapies are associated with an increased risk of breast and uterine cancer as well as cardiovascular risks, and thus, they are either not recommended or are recommended temporarily only for short treatment durations to manage menopausal symptoms such as hot flushes and sweats.

Estriol has been used extensively in Europe and Asia at 0.5 mg to 2 mg per day for 3 to 6 month treatment durations for hot flushes and sweats, but no effect on neuroprotection or prevention of cognitive decline has been shown during these short treatment durations. Estriol treatment would be required for at least a year and likely more than 3 years to have measurable neuroprotective effects in slowing, preventing, or reversing cognitive decline and dementia during menopause. In some aspects, the invention relates to prolonged treatment (e.g., at least 6 months, at least one year, or at least two or more years) with estriol with the addition of a progestogen to protect against uterine endometrial hyperplasia, because progestogens can forestall or even prevent endometrial hyperplasia induced by long-term estrogen use. The dose and type of progestogen to be used with estriol treatment for relatively long treatment durations is provided. The progestogen type, dose, and duration is important for methods reducing the progression of cognitive decline, memory loss, and/or learning disability because some progestogen treatments can counteract the beneficial effects of estrogen on the brain, including its potential beneficial effect on cognitive performance.

Methods of Using Estrogens to Reduce One or More Symptoms of Menopause

The term "estrogen" as used herein refers to any biologically active form of estrogen or precursor thereof. The term "estrogen" thus embraces naturally occurring, synthetic, and semi-synthetic forms of estrogen, and biologically active, pharmaceutically acceptable salts and esters thereof. In certain embodiments, estrogen is selected from estriol (E3), estradiol (E2), estrone (E1), an ester thereof, a pharmaceutically acceptable salt of an ester thereof, and any combination of the foregoing. In certain embodiments, estrogen is estriol (E3) or an ester thereof, or a pharmaceutically acceptable salt of an ester thereof. For example, the estrogen can be estriol, estriol succinate, estriol dihexanoate, or estriol sulfate. In other embodiments, estrogen is estradiol (E2) or an ester thereof, or a pharmaceutically acceptable salt of an ester thereof, while in yet other embodiments, estrogen is estrone (E1) or an ester thereof, or a pharmaceutically acceptable salt of an ester thereof. In certain preferred embodiments, estrogen is estriol (E3). In certain embodiments, estrogen is estradiol (E2). In certain embodiments, estrogen is estrone (E 1).

In certain embodiments, the estrogen is administered in a dose equal or equivalent to about 200 µg to about 20 mg estriol daily. For example, a dose of 2 mg to 8 mg of estriol is generally considered to be equivalent to 0.6 to 2.5 mg of conjugated estrogens or estrone. In certain embodiments, the estrogen is administered in a dose equal or equivalent to about 1 mg to about 10 mg estriol daily, preferably equal or equivalent to about 2 mg to about 8 mg estriol daily. In most preferred embodiments, the estrogen is estriol administered in a dose of about 2 mg, about 4 mg, about 6 mg, or about 8 mg of estriol daily.

In certain embodiments, the estrogen is formulated for oral administration, e.g., in a dose equal or equivalent to about 200 µg to about 20 mg estriol daily. For example, a dose of 2 mg to 8 mg of estriol is generally considered to be equivalent to 0.6 mg to 2.5 mg of conjugated estrogens or estrone. In certain embodiments, the estrogen is formulated for oral administration in a dose equal or equivalent to about 1 mg to about 10 mg estriol daily, preferably equal or equivalent to about 2 mg to about 8 mg estriol daily. In most preferred embodiments, the estrogen is estriol formulated for oral administration in a dose of about 2 mg, about 4 mg, about 6 mg, or about 8 mg of estriol daily.

In certain embodiments, the estrogen is orally administered in a dose equal or equivalent to about 200 µg to about 20 mg estriol daily. For example, a dose of 2 mg to 8 mg of estriol is generally considered to be equivalent to 0.6 mg to 2.5 mg of conjugated estrogens or estrone. In certain embodiments, the estrogen is orally administered in a dose equal or equivalent to about 1 mg to about 10 mg estriol daily, preferably equal or equivalent to about 2 mg to about 8 mg estriol daily. In most preferred embodiments, the estrogen is estriol orally administered in a dose of about 2 mg, about 4 mg, about 6 mg, or about 8 mg of estriol daily.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of menopause.

A therapeutically effective dose of the estrogen is, in some embodiments, one sufficient to raise the serum concentration above basal levels, and preferably to pregnancy levels or above pregnancy levels. In certain embodiments, the therapeutically effective dose of the estrogen is selected to result in serum levels in a patient equivalent to the steroid hormone level of that agent in women in the second or third trimester of pregnancy.

For example, during the normal female menstrual cycle estradiol levels are in the range of about 350 pg/ml serum. During pregnancy, there is about a 100-fold increase in the level of estradiol to about 10,000 to about 35,000 pg/ml serum. Correale et al., *J Inmmunol* 161:3365-74 (1998) and Gilmore et al., *J Immunol* 158:446-51 (1997). In contrast, estriol levels are undetectable during the menstrual cycle in the non-pregnant state. Estradiol levels rise progressively during pregnancy to levels from 3,000 to 30,000 pg/ml (3 to 30 ng/ml).

In one embodiment, where the estrogen is estriol, the dose is from about 1 mg to about 8 mg daily, and more specifically, about 2 mg, about 3 mg, about 4 mg, about 5 mg, about 6 mg, about 7 mg, or about 8 mg daily. In this embodiment, blood serum levels preferably reach at least about 0.5 ng/ml, may reach about 3 ng/ml to about 20 ng/ml, or most preferably about 5-8 ng/ml. In some embodiments, estradiol (E2) levels would preferably reach at least about 20 pg/ml and most preferably about to 40 pg/ml to 8,000 pg/ml. In some embodiments, estrone (E1) levels would preferably reach at least about 3 ng/ml and most preferably about 4 ng/ml to 16 ng/ml.

The dosage of the estrogen may be selected for an individual patient depending upon the route of administration, severity of disease, age and weight of the patient, other medications the patient is taking and other factors normally considered by the attending physician, when determining the individual regimen and dosage level as the most appropriate for a particular patient. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected. In vitro or in vivo assays can be employed to help identify optimal dosage ranges.

The therapeutically effective dose of the estrogen included in the dosage form is selected at least by considering the type of estrogen selected and the mode of administration. The dosage form may include the estrogen in combination with other inert ingredients, including adjuvants and pharmaceutically acceptable carriers for the facilitation of dosage to the patient as known to those skilled in the pharmaceutical arts. The dosage form may be any form suitable to cause the estrogen to enter into the tissues of the patient.

Pharmaceutically acceptable carriers can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can include, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. Any agent described herein, if desired, can also comprise minor amounts of wetting or emulsifying agents, or pH buffering agents.

In one embodiment, the dosage form of the estrogen is an oral preparation (liquid, tablet, capsule, caplet, gelcap, or the like) which when consumed results in elevated serum estrogen levels. The oral preparation may comprise conventional carriers including diluents, binders, time-release agents, lubricants, and disintegrants.

In other embodiments of the invention, the dosage form of the estrogen may be provided in a topical preparation (lotion, cream, ointment, patch, or the like) for transdermal application.

Alternatively, the dosage form may be provided as a suppository or the like for transvaginal or transrectal application.

However, in other embodiments, the dosage form may also allow for preparations to be applied subcutaneously, intravenously, intramuscularly, or via the respiratory system.

The term "progestogen" (also known as "gestagen") as used herein refers to any steroid hormone that binds to and activates a progesterone receptor, or a precursor thereof. The term "progestogen" thus embraces naturally occurring, synthetic, and semi-synthetic forms of progestogen, and biologically active, pharmaceutically acceptable salts and esters thereof.

In certain embodiments, the progestogen is selected from chlormadinone acetate, cyproterone acetate, desogestrel, dienogest, 5α-dihydroprogesterone, drospirenone (Yasmin®), ethinodiol acetate, ethynodiol diacetate, etonogestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol, megestrol acetate (17α-acetoxy-6-dehydro-6-methylprogesterone), nestorone, nomegestrol acetate, norethindrone, norethindrone acetate (also known as norethisterone acetate), norethynodrel (Enovid®), norgestimate, norgestrel, progesterone, tanaproget, trimegestone, or a pharmaceutically acceptable salt of any of the foregoing, or any combination thereof.

In certain embodiments, progestogen is a progestin. The term "progestin" as used herein refers to a synthetic progestogen as defined herein. Examples of progestins include desogestrel, dienogest, drospirenone (Yasmin®), ethinodiol acetate, etonogestrel (Nexplanon®), gestodene, levonorgestrel (Alesse®), medroxyprogesterone acetate (Provera®), nestorone, nomegestrol acetate, norethindrone, norethindrone acetate, norethynodrel (Enovid®), norgestimate, norgestrel, and trimegestone.

In certain embodiments, the progestogen is selected from progesterone, 17-hydroxyprogesterone, 5α-dihydroprogesterone, norethindrone, norethindrone acetate (also known as norethisterone acetate), medroxyprogesterone acetate (17α-hydroxy-6α-methylprogesterone acetate), megestrol acetate (17α-acetoxy-6-dehydro-6-methylprogesterone), desogestrel, levonorgestrel, chlormadinone acetate, and cyproterone acetate, pharmaceutically acceptable salts of any of the foregoing, and any combination thereof. In certain embodiments, progestogen is selected from progesterone, 17-hydroxyprogesterone, 5α-dihydroprogesterone, norethindrone, norethindrone acetate (also known as norethisterone acetate), desogestrel, levonorgestrel, chlormadinone acetate, and cyproterone acetate, pharmaceutically acceptable salts and esters of any of the foregoing, and any combination thereof. In certain embodiments, progestogen is norethindrone or an ester thereof, or a pharmaceutically acceptable salt of an ester thereof, preferably norethindrone. In certain embodiments, progestogen is progesterone or an ester thereof, or a pharmaceutically acceptable salt of an ester thereof.

In certain embodiments, the progestogen is administered in a dose equal or equivalent to about 70 µg to about 7 mg norethindrone daily, such as about 100 µg to about 1 mg norethindrone daily, most preferably in a dose equal or equivalent to about 0.7 mg norethindrone daily. In certain preferred embodiments, the progestogen is norethindrone administered in a dose of 0.7 mg norethindrone daily.

In certain embodiments, the progestogen is formulated for oral administration, e.g., in a dose equal or equivalent to about 70 µg to about 7 mg norethindrone daily, such as about 100 µg to about 1 mg norethindrone daily, most preferably in a dose equal or equivalent to about 0.7 mg norethindrone daily. In certain preferred embodiments, the progestogen is norethindrone formulated for oral administration in a dose of 0.7 mg norethindrone daily.

In certain embodiments, the progestogen is orally administered in a dose equal or equivalent to about 70 µg to about 7 mg norethindrone daily, such as about 100 µg to about 1 mg norethindrone daily, most preferably in a dose equal or equivalent to about 0.7 mg (i.e., 700 µg) norethindrone daily. In certain preferred embodiments, the progestogen is norethindrone orally administered in a dose of 0.7 mg (i.e., 700 µg) norethindrone daily.

The therapeutically effective dose of the progestogen included in the dosage form can be selected at least by considering the type of progestogen selected and the mode of administration. The dosage form may include the progestogen in combination with other inert ingredients, including adjuvants and pharmaceutically acceptable carriers for the facilitation of dosage to the patient as known to those skilled in the pharmaceutical arts. The dosage form may be any form suitable to cause the progestogen to enter into the tissues of the patient.

In one embodiment, the dosage form of the progestogen is an oral preparation (liquid, tablet, capsule, caplet, or the like) which when consumed results in elevated serum progestogen levels. The oral preparation may comprise conventional carriers including diluents, binders, time-release agents, lubricants, and disintegrants.

In other embodiments of the invention, the dosage form of the progestogen may be provided in a topical preparation (lotion, cream, ointment, patch, or the like) for transdermal application.

Alternatively, the dosage form may be provided as a suppository or the like for transvaginal or transrectal application.

The estrogen is administered to the subject on a continuous basis throughout two or more consecutive treatment periods. In certain embodiments a continuous basis means daily, i.e., on consecutive days. For example, estrogen administered orally to a subject on a daily basis throughout two or more consecutive treatment periods is deemed to be estrogen administered to the subject on a continuous basis throughout two or more consecutive treatment periods. Alternatively, estrogen administered transdermally to a subject on a daily basis throughout two or more consecutive treatment periods is deemed to be estrogen administered to the subject on a continuous basis throughout two or more consecutive treatment periods.

As used herein, a "treatment period" refers to a period of time during which a subject is receiving, on a continuous or daily basis, at least one therapeutic agent administered for the purpose of treating MS in the subject. In certain embodiments, each treatment period is at least 28 consecutive days. In certain embodiments, each treatment period is at least 56 consecutive days. In certain embodiments, each treatment period is at least 84 consecutive days. In certain embodiments, each treatment period is at least 112 consecutive days. In certain embodiments, each treatment period is at least 140 consecutive days. In certain embodiments, each treatment period is at least 168 consecutive days.

In certain embodiments, each treatment period is at least 4 consecutive weeks. In certain embodiments, each treatment period is at least 8 consecutive weeks. In certain embodiments, each treatment period is at least 12 consecutive weeks. In certain embodiments, each treatment period is at least 16 consecutive weeks. In certain embodiments, each treatment period is at least 20 consecutive weeks. In certain embodiments, each treatment period is at least 24 consecutive weeks.

In certain embodiments, each treatment period is at least one month. In certain embodiments, each treatment period is at least two consecutive months. In certain embodiments, each treatment period is at least three consecutive months. In certain embodiments, each treatment period is at least four consecutive months. In certain embodiments, each treatment period is at least five consecutive months. In certain embodiments, each treatment period is at least six consecutive months.

The progestogen is administered to the subject for only a portion of each treatment period. As used herein, "for only a portion of each treatment period" refers generally to a period of time that occurs during but is at least one day shorter than a treatment period. In a preferred embodiment, the phrase "for only a portion of each treatment period" refers generally to a period of consecutive days that occurs during but is at least one day shorter than a treatment period.

In certain embodiments, the portion of each treatment period is daily for all but at least 7 consecutive days of each treatment period. For example, if the treatment period is 28 days, in various embodiments the portion of such treatment period can be 1, 2, 3, 4, 5, 6, 7, 8, 9, 10, 11, 12, 13, 14, 15, 16, 17, 18, 19, 20, or 21 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, or 1 to 21.

In certain embodiments, the portion of each treatment period is daily for all but at least 14 consecutive days of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14.

In certain embodiments, the portion of each treatment period is daily for up to 7 consecutive days of each treatment period. For example, if the treatment period is 28 days, in various embodiments the portion of such treatment period can be 1, 2, 3, 4, 5, 6, or 7 consecutive days. For convenience, such portion can begin on day 1 of a treatment period, such that, for this example, the portion can encompass day 1 or days 1 to 2, 1 to 3, 1 to 4, 1 to 5, 1 to 6, or 1 to 7.

In certain embodiments, the portion of each treatment period is daily for up to 14 consecutive days of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, to 7, 1 to 8, 1 to 9, to 10, 1 to 1 to 12, 1 to 13, or 1 to 14.

In certain embodiments, the portion of each treatment period is daily for all but at least half of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14.

Preferably the progestogen is administered to the subject for only a portion of each treatment period. During the remainder of the treatment period, in certain embodiments the subject can receive estrogen but neither progestogen nor a placebo in place of the progestogen. Alternatively, during the remainder of the treatment period, in certain embodiments the subject can receive both estrogen and a placebo in place of the progestogen.

An aspect of the invention is a method of reducing one or more symptoms of menopause in a female subject. The method includes the steps of administering orally to a subject in need thereof, on a continuous basis for 84 consecutive days (12 weeks), about 2 mg to about 8 mg of estriol daily (e.g., such as about 2 mg, about 3 mg, about 4 mg, about 5 mg, about 6 mg, about 7 mg, or about 8 mg of estriol daily); and administering orally to the subject, for 14 consecutive days (2 weeks) of the 84 consecutive days (12 weeks), about 0.7 mg of progestogen daily. In certain embodiments, the 14 consecutive days (2 weeks) are the first 14 consecutive days (2 weeks) of the 84 consecutive days (12 weeks). That is, if the 84 consecutive days of estrogen administration are deemed to start on day 1, the progestogen is administered on days 1, 2, 3, 4, 5, 6, 7, 8, 9, 10, 11, 12, 13, and 14, and then stopped. In certain embodiments, the subject may then continue to receive estrogen but neither progestogen nor a placebo in place of the progestogen for the remaining 70 days. In other embodiments, the method further includes the step of administering to the subject a placebo in place of the progestogen on each of the days the progestogen is not administered to the subject. That is, the subject may then receive both estrogen and a placebo in place of the progestogen for the remaining 70 days. In some embodiments, the one or more symptoms of menopause comprise impaired cognitive function and/or cognitive decline. In some embodiments, the one or more symptoms of menopause comprise impaired memory and/or learning.

An aspect of the invention is a method of reducing one or more symptoms of menopause in a female subject. The method includes the steps of administering orally to a subject in need thereof, on a continuous basis for 84 consecutive days (12 weeks), about 2 mg to about 8 mg of estriol daily (e.g., such as about 2 mg, about 3 mg, about 4 mg, about 5 mg, about 6 mg, about 7 mg, or about 8 mg of estriol daily); and administering orally to the subject, for 14 consecutive days (2 weeks) of the 84 consecutive days (12 weeks), about 0.7 mg of norethindrone daily. In certain embodiments, the 14 consecutive days (2 weeks) are the first 14 consecutive days (2 weeks) of the 84 consecutive days (12 weeks). That is, if the 84 consecutive days of estrogen administration are deemed to start on day 1, the norethindrone is administered on days 1, 2, 3, 4, 5, 6, 7, 8, 9, 10, 11, 12, 13, and 14, and then stopped. In certain embodiments, the subject may then continue to receive estrogen but neither norethindrone nor a placebo in place of the norethindrone for the remaining 70 days. In other embodiments, the method further includes the step of administering to the subject a placebo in place of the norethindrone on each of the days the norethindrone is not administered to the subject. That is, the subject may then receive both estrogen and a placebo in place of the norethindrone for the remaining 70 days.

The term "subject" as used herein refers to a living primate and may be interchangeably used with the term "patient". In certain embodiments, the subject is a human. Preferably, the human subject is female, such as a woman, most preferably a peri-menopausal or post-menopausal woman. The subject may present with cognitive impairment, e.g., mild cognitive impairment. In some embodiments, the subject does not present with cognitive impairment, e.g., the subject does not present with mild cognitive impairment. In some embodiments, the patient does not have multiple sclerosis or the patient has not been diagnosed with multiple sclerosis. In some embodiments, the patient does not have a Th1 mediated autoimmune disease or the patient has not been diagnosed with a Th1 mediated autoimmune disease. In some embodiments, the patient does not have a neurodegenerative autoimmune disease or the patient has not been diagnosed with a neurodegenerative autoimmune disease. In some embodiments, the patient does not have an autoimmune disease or the patient has not been diagnosed with an autoimmune disease. In some embodiments, the patient does not have a neurodegenerative disease or the patient has not been diagnosed with a neurodegenerative disease.

In certain embodiments, the estrogen and the progestogen are formulated separately from one another, e.g., the subject receives the estrogen as a single formulation and the progestogen as a separate formulation. For oral administration, a given dose of each formulation can comprise one or more pills, tablets, capsules, gelcaps, or the like (i.e., unit doses). For example, an 2 mg dose of estriol can be administered as two 1 mg capsules, and a 0.7 mg dose of norethindrone can be administered as a single capsule, though preferably each dose is administered in a single unit dose (e.g., one unit dose each for the estrogen and the progestogen). Similarly, an 8 mg dose of estriol can be administered as two 4 mg capsules, and a 0.7 mg dose of norethindrone can be administered as a single capsule, though preferably each dose is administered in a single unit dose (e.g., one unit dose each for the estrogen and the progestogen).

In certain embodiments, e.g., where a placebo is administered with the estrogen on days when progestogen is not administered, the estrogen and the placebo are formulated separately from one another. For example, the subject is administered the estrogen as a single formulation and the placebo as a separate formulation. For oral administration, a given dose of each formulation can comprise one or more pills, tablets, capsules, gelcaps, or the like (i.e., unit doses). For example, a 2 mg dose of estriol can be administered as two 1 mg capsules, and a placebo can be administered as a single capsule. Similarly, an 8 mg dose of estriol can be administered as two 4 mg capsules, and a placebo can be administered as a single capsule.

When a given dose of any agent involves administration of more than a single unit dose, e.g., two 1 mg capsules (or two 4 mg capsules) of estriol, the individual unit doses can be administered at essentially the same time, or they can be administered at different times on a given day, provided the entire daily dose is administered within a single day. For example, two 1 mg capsules (or two 4 mg capsules) of estriol can be taken together essentially once a day, or they may be taken one at a time twice a day. Additional schedules are contemplated by the invention, again provided the entire daily dose is administered within a single day. While it may be preferable that the subject follow the same schedule from one day to the next, such is not required, once again provided the entire daily dose is administered within a single day.

When the estrogen and the progestogen are formulated separately, they can be administered essentially simultaneously, or they can be administered sequentially with respect to each other. For example, in one embodiment the subject is administered two 1 mg capsules (or two 4 mg capsules) of estriol and one 0.7 mg capsule of norethindrone essentially simultaneously. In another embodiment, the subject is administered estriol in divided doses, e.g., one 1 mg capsule twice daily (or one 4 mg capsule twice daily), and the progestogen is administered essentially simultaneously with one of the divided doses of estriol. In yet another embodiment, the subject is administered estriol in divided doses, e.g., one 1 mg capsule twice daily (or one 4 mg capsule twice daily), and the progestogen is administered at a separate time from either one of the divided doses of estriol.

Similarly, when the estrogen and the placebo are formulated separately, they can be administered essentially simultaneously, or they can be administered sequentially with respect to each other. For example, in one embodiment the subject is administered two 1 mg capsules (or two 4 mg capsules) of estriol and one placebo essentially simultaneously. In another embodiment, the subject is administered estriol in divided doses, e.g., one 1 mg capsule twice daily (or one 4 mg capsule twice daily), and the placebo is administered essentially simultaneously with one of the divided doses of estriol. In yet another embodiment, the subject is administered estriol in divided doses, e.g., one 1 mg capsule twice daily (or one 4 mg capsule twice daily), and the placebo is administered at a separate time from either one of the divided doses of estriol.

In certain embodiments, the estrogen and the progestogen are formulated together. For oral administration, a given dose of each component, formulated together, can comprise one or more pills, tablets, capsules, or the like (i.e., unit doses). For example, a 2 mg dose of estriol and a 0.7 mg dose of norethindrone can be coformulated and administered as two capsules, each containing 1 mg estriol and 0.35 mg norethindrone, though preferably, where applicable, they are coformulated as one unit dose comprising both the estrogen and the progestogen. Similarly, an 8 mg dose of estriol and a 0.7 mg dose of norethindrone can be coformulated and administered as two capsules, each containing 4 mg estriol and 0.35 mg norethindrone, though preferably, where applicable, they are coformulated as one unit dose comprising both the estrogen and the progestogen.

In certain embodiments, e.g., where a placebo is administered with the estrogen on days when progestogen is not administered, the estrogen and the placebo are formulated together. For oral administration, a given dose of each component, formulated together, can comprise one or more pills, tablets, capsules, or the like (i.e., unit doses). For example, a 2 mg dose of estriol and a placebo can be coformulated and administered as two capsules, each containing 1 mg estriol and a suitable amount of placebo. Similarly, an 8 mg dose of estriol and a placebo can be coformulated and administered as two capsules, each containing 4 mg estriol and a suitable amount of placebo.

When a given dose of any coformulation of estriol and progestogen (or placebo) involves administration of more than a single unit dose, e.g., two capsules, each containing 1 mg estriol and 0.35 mg norethindrone, the individual unit doses can be administered at essentially the same time, or they can be administered at different times on a given day, provided the entire daily dose is administered within a single day. For example, two capsules, each containing estriol and progestogen (or placebo) can be taken together essentially once a day, or they may be taken one at a time twice a day. Additional schedules are contemplated by the invention, again provided the entire daily dose is administered within a single day. While it may be preferable that the subject follow the same schedule from one day to the next, such is not required, once again provided the entire daily dose is administered within a single day.

Cognitive Ability

In some embodiments, subjects are tested prior to treatment to obtain a global cognitive function using the Mini Mental Status Exam (MMSE) and well as for performance in four specific areas including 1) verbal memory, 2) visual memory, 3) language, and 4) attention/processing speed (Table 1). The MMSE may also be used, for example, to assess the memory and/or learning ability of a subject. Representative tests within each of the specific areas are shown below. Raw scores may be adjusted for age and education for each test as is standard in the field. Similar tests may be used for each specific cognitive area either in combination or instead of those listed in Table 1. Nevertheless, the same test is preferably employed for each area within the same individual longitudinally over time because the comparison of different tests, even within the same cognitive area, will lower the sensitivity to detect change.

TABLE 1

Cognitive Testing Brief Repeatable Battery (with options for cognitive areas)

| | |
|---|---|
| Verbal memory | 1. Buschke Selective Reminding Test (SRT) (Buschke & Fuld) |
| |    a. Long Term Storage (LTS) |
| |    b. Consistent Long Term Retrieval (CLTR) |
| | 2. Verbal Paired Associates-Wechsler Memory Scale, 3rd ed (WMS-III) |
| |    a. Learning Trials (1-4) |
| |    b. Delayed Recall Score |
| Visual Memory | 1. The 10/36 Spatial Recall Test (SPART 10/36) (Barbizet) |
| |    a. Total number correct in 5 learning trials (SPART trials 1-5, set A) |
| |    b. Number of correct responses for interfering set B (SPART trial B) |

TABLE 1-continued

Cognitive Testing Brief Repeatable Battery (with options for cognitive areas)

|  |  |
| --- | --- |
|  | c. Number of correct for recall of set A (SPART trial A recall) |
|  | d. Number of correct responses for delayed recall (delayed SPART 10/36) |
|  | 2. Benton, Forms C, D, E (Benton 1955, Amieva, Gaestel, et al 2006) |
|  | a. Visuospatial working memory |
|  | b. 15 trials; possible score 0-5 |
| Language | 1. Word List Generation (WLG)-Verbal Fluency (Rao, 1990) |
|  | a. Total words generated in 60 seconds |
| Attention/Speed of Information Processing | 1. Paced Auditory Serial Addition test (PASAT)-number correct out of 60 trials |
|  | a. 3 second interval (PASAT 3') |
|  | b. 2 second interval (PASAT 2') |
|  | 2. Symbol Digit Modalities (SDMT) (Smith, 1991) |
|  | a. Number correct in 90 seconds |

In some embodiments, cognitive testing is repeated periodically, such as at one year intervals. For example, cognitive testing may be repeated annually for one, two, three, four, five, six, seven, eight, nine, ten, or more years. After repeating the test over one or more years, an assessment regarding whether a subject's cognitive test scores have remained stable or declined may be made by plotting scores over time. Cognition may be determined to have remained stable, for example, if a subject's scores have remained stable in the MMSE as well as in 3 of the 4 specific cognitive test areas. In some embodiments, patients with stable cognitive test scores will remain on estriol treatment and such subjects may optionally begin a new cycle of testing.

In some embodiments, an assessment may be moved to an earlier date, for example, if other evidence suggests that the subject has experienced cognitive decline, memory loss, and/or progression of a learning disability.

In some embodiments, a subject's dose of an estrogen may be increased if the subject's cognitive scores decline. For example, the dose of estrogen may be increased from 2 mg estriol per day to 4 mg per day while keeping the dose of the progestogen unchanged. Similarly, the dose of estrogen may be increased from 4 mg estriol per day to 8 mg per day while keeping the dose of the progestogen unchanged. A decline in cognitive score may be determined, for example, if the subject's cognitive scores are significantly worse on the MMSE and in 2 or more of the 4 specific cognitive areas. In some embodiments, cognitive decline, learning disability, and/or memory loss may be confirmed, for example, by retesting a subject. In such embodiments, a subject may be retested within one month after an original assessment of cognitive decline, learning disability, and/or memory. Subjects who display cognitive decline, learning disability, and/or memory may be referred to a neurologist for further evaluation of the decline. In some embodiments, a decision may be made to continue or cease the administration of an estrogen based on the evaluation of a neurologist and/or based on the subject's other menopausal symptoms. In some embodiments, the dose of estrogen may be increased if no other disease processes are identified by the neurologist in a subject with confirmed cognitive decline, learning disability, and/or memory. For example, the dose of estrogen may be increased from 2 mg estriol per day to 4 mg per day while keeping the dose of the progestogen unchanged. Similarly, the dose of estrogen may be increased from 4 mg estriol per day to 8 mg per day while keeping the dose of the progestogen unchanged.

In embodiments in which the subject displays cognitive decline, learning disability, and/or memory, a one-year assessment cycle may follow any dose adjustment. The one-year assessment may comprise testing 3 times over one year, for example, testing before dose adjustment, testing 6 months after dose adjustment, and testing 12 months after dose adjustment. Such testing may be used to determine whether a dose adjustment has affected the cognitive decline, learning disability, and/or memory of the subject.

Safety is measured based on neurologic exams, laboratory tests (chemistries, complete blood count (CBC)), and breast and gynecologic exams. In some embodiments, the dose of the estrogen may be decreased, for example, if the subject displays a symptom or condition that might be a side effect caused by estrogen. For example, the dose of an estrogen may be decreased from 8 mg estriol per day to 4 mg estriol per day while the progestogen dose remains the same. Similarly, the dose of an estrogen may be decreased from 2 mg estriol per day to 1 mg estriol per day while the progestogen dose remains the same.

Products Comprising an Estrogen and a Progestogen

Figure 2A:
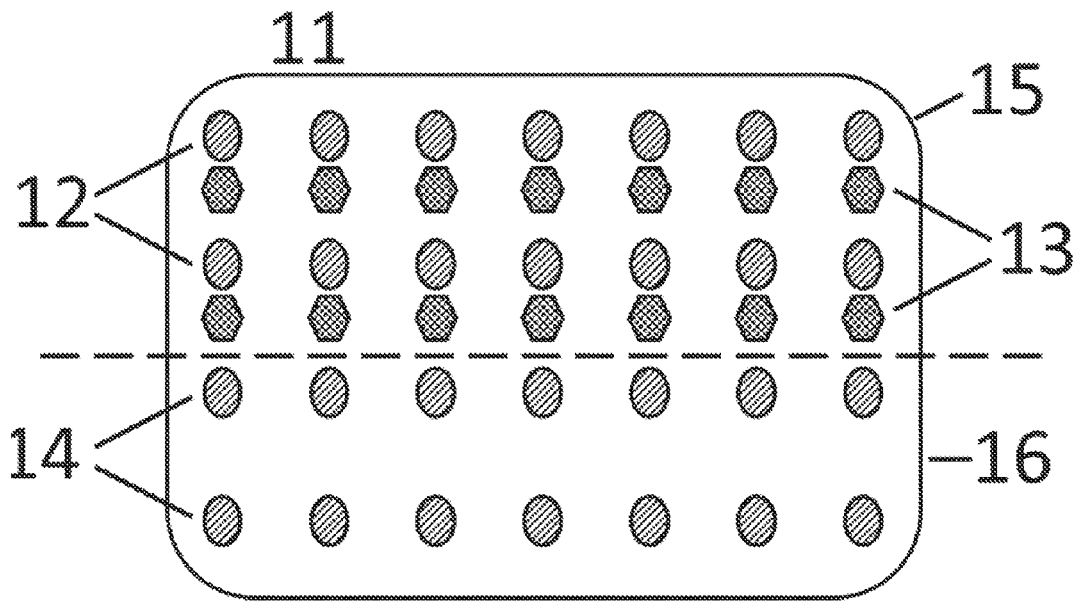
FIGS. 2A and 2B depicts an embodiment of the packaged pharmaceutical product described herein, comprising a first support structure 11; a first region 15 comprising a first series of doses of an estrogen 12 and each dose of progestogen with which the first series of doses of estrogen are associated 13; a second region 16 comprising a second series of doses of the estrogen 14; and a second support structure 17.
Figure 2B:
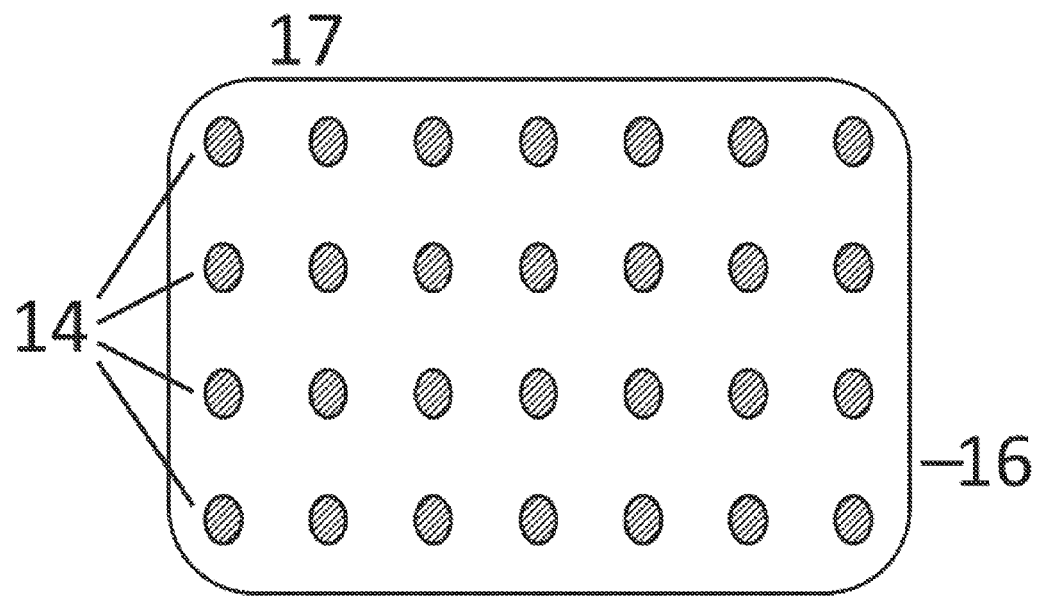

In some aspects, the invention relates to novel packaged pharmaceutical products for the treatment of menopause. FIGS. 2A and 2B depict an embodiment of the packaged pharmaceutical product described herein, comprising a first support structure 11 and a second support structure 17. The first support structure 11 comprises a first region 15 comprising a first series of fourteen doses of estrogen 12, and each dose of the estrogen is associated with a dose of a progestogen 13.

The first support structure 11 also comprises a portion of the second region 16, wherein the second region comprises a second series of doses of estrogen 14. Additionally, the second support structure 17 comprises a portion of the second region 16. As depicted in FIG. 2, the entire second region, over both support structures, comprises at least forty-two doses of estrogen. FIG. 2 depicts that fourteen doses of estrogen from the second region 16 are held by the first support structure 11 and twenty-eight doses of estrogen from the second region 16 are held by the second support structure 17. In preferred embodiments, the product comprises a third support structure identical to the second support structure 17 depicted in FIG. 2B, to provide an additional twenty-eight doses of estrogen from the second region 16, such that the second region 16, over all three support structures, comprises seventy total doses of the estrogen, in accordance with embodiments disclosed herein where the administration cycle is 84 days. In certain embodiments, such as where the product provides sufficient doses for two or more administration cycles, the product may comprise multiple sets of support structures as described above, one set for each administration cycle.

The first support structure 11 comprises a first grid that consists of seven columns and four rows. The first series of doses of the estrogen 12, each with its associated dose of progesterone 13, constitutes the first two rows. The use of seven columns permits the user to easily associate each column with a day of the week, in analogy with a calendar.

The intersection of a row and a column defines a position for locating one or two chambers. In certain embodiments, each position in the first and second rows of the first support structure 11 comprises two chambers, wherein one dose of the estrogen from the first series 12 occupies a first chamber at each position and its associated dose of the progestogen occupies a second chamber at each position. Preferably, though, each position in the first and second rows comprises a single chamber that holds both the dose of estrogen and the dose of progestogen. Each position in the third and fourth rows of the first support structure 11 comprises one chamber, wherein one dose of the estrogen from the second series 14 occupies the chamber at each position. Each position in the second support structure 17 comprises one chamber, wherein one dose of the estrogen from the second series 14 occupies the chamber at each position.

Figure 3A:
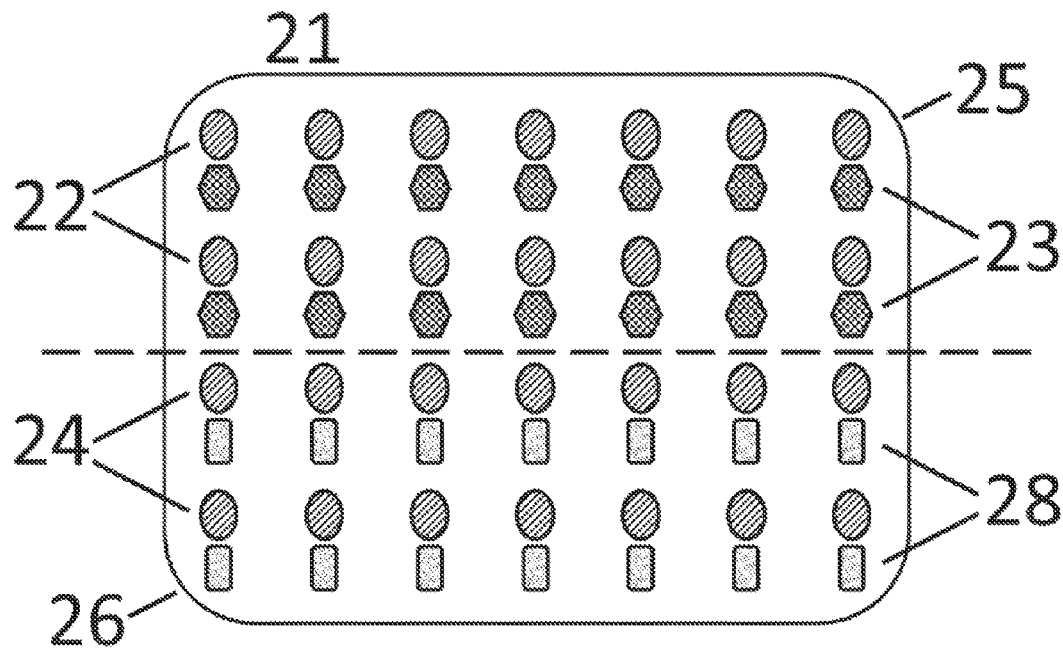
FIGS. 3A and 3B depicts an embodiment of the packaged pharmaceutical product described herein, comprising a first support structure 21; a first region 25 comprising a first series of doses of an estrogen 22 and each dose of progestogen with which the first series of doses of estrogen are associated 23; a second region 26 comprising a second series of doses of the estrogen 24 and each dose of placebo with which the second series of doses of estrogen are associated 28; and a second support structure 27.
Figure 3B:
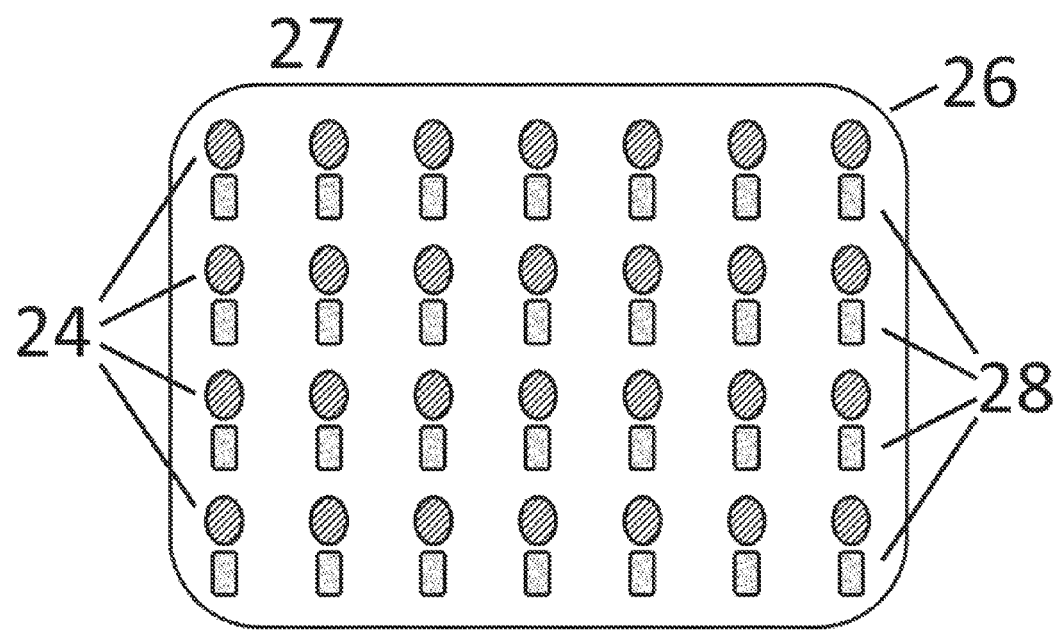

FIGS. 3A and 3B depict an embodiment of the packaged pharmaceutical product described herein, comprising a first support structure 21 and a second support structure 27. The first support structure 21 comprises a first region 25 comprising a first series of fourteen doses of estrogen 22, and each dose of the estrogen is associated with a dose of a progestogen 23.

The first support structure 21 also comprises a portion of the second region 26, wherein the second region comprises a second series of doses of estrogen 24, and each dose of the estrogen is associated with a dose of a placebo 28. Additionally, the second support structure 27 comprises a portion of the second region 26. As depicted in FIG. 3, the entire second region, over both support structures, comprises at least forty-two doses of estrogen and forty-two doses of placebo. FIG. 3 depicts that fourteen doses each of estrogen and placebo from the second series 24 are held by the first support structure 21 and twenty-eight doses each of estrogen and placebo from the second series 24 are held by the second support structure 27. In preferred embodiments, the product comprises a third support structure identical to the second support structure 27 depicted in FIG. 3B, to provide an additional twenty-eight doses each of estrogen and placebo from the second series 24, such that the second region 26, over all three support structures, comprises seventy total doses each of the estrogen and the placebo, in accordance with embodiments disclosed herein where the administration cycle is 84 days. In certain embodiments, such as where the product provides sufficient doses for two or more administration cycles, the product may comprise multiple sets of support structures as described above, one set for each administration cycle.

The first support structure 21 comprises a first grid that consists of seven columns and four rows. The first series of doses of the estrogen 22, each with its associated dose of progesterone 23, constitutes the first two rows. The use of seven columns permits the user to easily associate each column with a day of the week, in analogy with a calendar.

The intersection of a row and a column defines a position for locating one or two chambers. In certain embodiments, each position in the first and second rows of the first support structure 21 comprises two chambers, wherein one dose of the estrogen from the first region 22 occupies a first chamber at each position and one dose of the progestogen from the first region 22 occupies a second chamber at each position. Preferably, though, each position in the first and second rows comprises a single chamber that holds both the dose of estrogen and the dose of progestogen. In certain embodiments, each position in the third and fourth rows of the first support structure 21 and each position in the second support structure 27 comprise two chambers, wherein one dose of the estrogen from the second region 26 occupies a first chamber at each position and one dose of the placebo from the second region 26 occupies a second chamber at each position. Preferably, though, each position in the third and fourth rows of the first support structure and each position in the second (and, if present, third) support structure 27 comprise a single chamber that holds both the dose of estrogen and the dose of placebo.

In some embodiments, the invention relates to a packaged pharmaceutical product, comprising a first region comprising a first series of doses of an estrogen, wherein each dose of the estrogen is associated with (e.g., adjacent or proximal to, or even co-located with) a dose of a progestogen; and a second region comprising a second series of doses of the estrogen that are not associated with doses of the progestogen. In such embodiments, the first region comprises both (i) a first series of doses of an estrogen and (ii) each dose of the progestogen with which the doses of estrogen are associated. In some embodiments, each dose of the estrogen in the second region is associated with a dose of placebo. In such embodiments, the second region comprises both (i) a second series of doses of an estrogen and (ii) each dose of the placebo with which the doses of estrogen are associated, such as in the manner in which the doses of estrogen in the first series are associated with doses of the progestogen.

The various doses of estrogen and progesterone may each be unit doses, such as tablets, capsules, caplets, or other oral dosage forms. Each dose of progestogen may be coformulated with the dose of estrogen with which it is associated, e.g., as a combined unit dose.

The estrogen may be estradiol (E2), estriol (E3), estrone (E1), or a pharmaceutically acceptable salt of any of the foregoing, or any combination thereof. In preferred embodiments, the estrogen is estriol. In some embodiments, a dose of the estrogen comprises a dose equal or equivalent to about 200 μg to about 20 mg of estriol, such as a dose equal or equivalent to about 200 μg to about 8 mg of estriol, or a dose equal or equivalent to about 400 μg to about 4 mg of estriol. For example, a dose of the estrogen may comprise a dose equal or equivalent to about 200 μg, 300 μg, 400 μg, 500 μg, 600 μg, 700 μg, 800 μg, 900 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In preferred embodiments, a dose of the estrogen comprises a dose equal or equivalent to about 800 μg to about 16 mg of estriol. In more preferred embodiments, a dose of the estrogen comprises a dose equal or equivalent to about 2 mg to about 8 mg of estriol. In some embodiments, a dose of the estrogen comprises 2 mg, 3 mg, 4 mg, 5 mg, 6 mg, 7 mg, or 8 mg of estriol.

The progestogen may be a progestin. In some embodiments, the progestogen is progesterone, 17-hydroxyprogesterone, 5α-dihydroprogesterone, norethindrone (also known as norhisterone), norethindrone acetate (also known as norhisterone acetate), desogestrel, levonorgestrel (Alesse®), medroxyprogesterone acetate (17α-hydroxy-6α-methylprogesterone acetate; Provera®), megestrol acetate (17α-acetoxy-6-dehydro-6-methylprogesterone), chlormadinone acetate, cyproterone acetate, norethynodrel (Enovid®), ethynodiol diacetate, norgestrel, gestodene, norgestimate, dienogest, drospirenone (Yasmin®), etonogestrel (Nexplanon®), nestorone, nomegestrol acetate, trimegestone, or tanaproget, or a pharmaceutically acceptable salt of any of the foregoing, or any combination thereof. In other embodiments, the progestogen is In preferred embodiments, the progestogen is norethindrone. In some embodiments, the progestogen comprises a dose equal or equivalent to about 70 µg to 7 mg of norethindrone. For example, a dose of the progestogen may comprise a dose equal or equivalent to about 100 µg, 200 µg, 300 µg, 400 µg, 500 µg, 600 µg, 700 µg, 800 µg, 900 µg, 1 mg, 2 mg, 3 mg, 4 mg, 5 mg, 6 mg, or 7 mg of norethindrone. In preferred embodiments, a dose of the progestogen comprises a dose equal or equivalent to about 100 µg to 1 mg of norethindrone. In more preferred embodiments, a dose of the progestogen comprises a dose equal or equivalent to about 700 µg of norethindrone. In some embodiments, a dose of the progestogen comprises 700 gig of norethindrone.

In some embodiments, each dose of the estrogen of the first series has a first color. In some embodiments, each dose of the estrogen of the second series has a second color. The first color and second color may be the same color. Alternatively, the first color and second color may be different colors. In some embodiments, each dose of the progestogen has a third color. In some embodiments, each dose of the placebo has a fourth color.

The product may comprise 28-365 doses of the estrogen. For example, the product may comprise 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 doses of the estrogen.

In some embodiments, the packaged pharmaceutical product comprises 5-84 doses of the progestogen. For example, the product may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 doses of the progestogen In some embodiments, the first region comprises 5-21 doses each of the estrogen and the progestogen. For example, the first region may comprise 5, 6, 7, 8, 9, 10, 11, 12, 13, 14, 15, 16, 17, 18, 19, 20, or 21 doses of the estrogen and an equal number of doses of the progestogen. In preferred embodiments, the first region comprises 14 doses each of the estrogen and the progestogen. In such embodiments, the first region comprises 14 doses of the estrogen and 14 doses of the progestogen.

In some embodiments, the second region comprises 7-90 doses of the estrogen. For example, the second region may comprise 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 doses of the estrogen. In preferred embodiments, the second region comprises 14 or 70 doses of the estrogen. In more preferred embodiments, the second region comprises 70 doses of the estrogen.

In some embodiments, successive doses of the estrogen in each series are associated with successive days of an administration cycle, and the administration cycle consists of 28-365 consecutive calendar days. For example, the administration cycle may consist of 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, or 365 consecutive calendar days. In certain embodiments, the administration cycle consists of 28 or 84 days. In preferred embodiments, the administration cycle consists of 84 days.

In some embodiments, the administration cycle consists of 4-52 weeks. For example, the administration cycle may consist of 4, 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. In certain embodiments, the administration cycle consists of 4 or 12 weeks. In preferred embodiments, the administration cycle consists of 12 weeks.

In some embodiments, the administration cycle consists of 1-12 months. For example, the administration cycle may consist of 1, 2, 3, 4, 5, 6, 7, 8, 9, 10, 11, or 12 months. In certain embodiments, the administration cycle consists of 1 or 3 months. In preferred embodiments, the administration cycle consists of 3 months.

In some embodiments, the administration cycle consists of 1 year.

In some embodiments, the product comprises one or more first regions and one or more second regions, arranged in an alternating sequence, that together provide a number of doses of the estrogen equal to the number of days in the administration cycle. For example, the product may consist of one first region and one second region. Alternatively, the product may consist of two first regions and two second regions or three first regions and three second regions. In other embodiments, the product consists of four first regions and four second regions.

In certain embodiments, the administration cycle consists of 28 consecutive calendar days; the first region comprises 14 doses each of the estrogen and the progestogen; and the second region comprises 14 doses of the estrogen. In certain embodiments, the second region also comprises 14 doses of the placebo.

In other embodiments, the administration cycle consists of 84 consecutive calendar days; the first region comprises 14 doses each of the estrogen and the progestogen; and the second region comprises 70 doses of the estrogen. In certain embodiments, the second region also comprises 70 doses of the placebo.

The product may consist of one first series of doses and one second series of doses, and the first series of doses may be associated with days of the administration cycle that precede the days associated with the second series of doses. Alternatively, the product may consist of one first series of doses and one second series of doses, and the second series of doses may be associated with days of the administration cycle that precede the days associated with the first series of doses.

In some embodiments, the product comprises markings designating each dose for the day of the administration cycle associated with that dose. The markings may designate each dose with a day of the week or month. For example, the markings may designate the first dose in a series of doses with a first day of the administration cycle, and the markings may designate successive doses of the series with consecutive days of the week or month. In some embodiments, the markings designate the first dose of a series with a Sunday in the administration cycle. In other embodiments, the markings designate the first dose of the first or second series with a Monday, Tuesday, Wednesday, Thursday, Friday, or Saturday in the administration cycle.

In certain embodiments, the doses of estrogen are each individually enclosed in a chamber, optionally together with any associated dose of progestogen or placebo.

In some embodiments, the product comprises a first support structure, wherein the first region occupies a portion of the first support structure. In some embodiments, the product comprises two or more support structures. The second region may be divided among two or more of the support structures. In some embodiments, the first region and at least part of the second region occupy adjacent portions of the first support structure. For example, the second region may occupy a portion of the first support structure, an entire second support structure, and an entire third support structure. In other embodiments, the first region and second region are disposed on separate support structures. For example, the first region may be disposed on the first support structure and the second region may be disposed on one or more different support structures.

In certain embodiments, the support structures comprise at least one grid; the at least one grid comprises seven columns and at least four rows; the intersection of one row and one column defines a position that optionally comprises one or two chambers; and one dose of the estrogen occupies one chamber at a plurality of positions on the grid. In other embodiments, the support structures comprise at least one grid; the at least one grid comprises seven columns and at least four rows; the intersection of one row and one column defines a position that comprises one or two chambers; and one dose of the estrogen occupies one chamber at each position.

In some embodiments, the first support structure comprises a first grid; the first grid comprises 7 columns and 4-16 rows; each dose of estrogen from the first series occupies a chamber at consecutive positions on the first grid; and the remaining positions in the first grid each comprise one chamber that is occupied by one dose of estrogen from the second region. In preferred embodiments, the first grid comprises 4 or 16 rows. In more preferred embodiments, the first grid comprises 4 rows. Each column may correspond to a day of the week. For example, the first column may correspond to Sunday, the second column may correspond to Monday, the third column may correspond to Tuesday, the fourth column may correspond to Wednesday, the fifth column may correspond to Thursday, the sixth column may correspond to Friday, and the seventh column may correspond to Saturday. Similarly, each row may correspond to a week of the administration cycle. For example, the first row may correspond to the first week of the administration cycle, the second row may correspond to the second week of the administration cycle, the third row may correspond to the third week of the administration cycle, the fourth row may correspond to the fourth week of the administration cycle, the fifth row may correspond to the fifth week of the administration cycle, the sixth row may correspond to the sixth week of the administration cycle, the seventh row may correspond to the seventh week of the administration cycle, the eighth row may correspond to the eighth week of the administration cycle, the ninth row may correspond to the ninth week of the administration cycle, the tenth row may correspond to the tenth week of the administration cycle, the eleventh row may correspond to the eleventh week of the administration cycle, the twelfth row may correspond to the twelfth week of the administration cycle, and so forth.

In some embodiments, each dose of estrogen from the first series occupies one chamber at consecutive positions in the first two rows of the first grid. For example, in preferred embodiments, the first series of doses of estrogen comprises 14 doses of estrogen; the first grid comprises 7 columns and 4 rows; and each of the 14 doses of estrogen from the first series occupies one chamber in the 14 positions defined by the 7 columns and the first two rows of the first grid. Additionally, in preferred embodiments, the first region comprises 14 doses of progestogen, which are associated with each dose of estrogen from the first series; the first grid comprises 7 columns and 4 rows; and each of the 14 doses of progestogen from the first region occupies one chamber in the 14 positions defined by the 7 columns and first two rows of the first grid. Each dose of progestogen may occupy the same chamber as the dose of estrogen with which the dose of progestogen is associated. Alternatively, each dose of progestogen may occupy a separate chamber at the same position as the dose of estrogen with which the dose of progestogen is associated.

In some embodiments, the packaged pharmaceutical product comprises a second support structure that comprises a second grid, wherein the second grid comprises 7 columns and 4-8 rows; and one dose of estrogen from the second series occupies one chamber at each position of the second grid. In preferred embodiments, the second support structure comprises 7 columns and 4 rows. In such embodiments, the first support structure may be associated with the first four weeks of an administration cycle and the second support structure may be associated with the second four weeks of the administration cycle.

In some embodiments, the packaged pharmaceutical product comprises comprising a third support structure and a third grid, wherein: the third grid comprises 7 columns and 4 rows; and one dose of estrogen from the second series occupies one chamber at each position of the third grid. In preferred embodiments, the third support structure comprises 7 columns and 4 rows. In such embodiments, the first support structure may be associated with the first four weeks of an administration cycle, the second support structure may be associated with the second four weeks of the administration cycle, and the third support structure may be associated with the third four weeks of the administration cycle.

The first grid, second grid, or third grid may defined by Cartesian coordinates or polar coordinates. Each grid may be a Cartesian grid, regular grid, polar grid, rectilinear grid, curvilinear grid, or structured grid. For example, the first grid, second grid, or third grid may be a square grid, rectangular grid, or circular grid.

In some embodiments, each support structure is a blister pack, blister card, or push-through-pack. In some embodiments, the chambers are rupturable chambers. In certain embodiments, the product is configured to separately release each dose of estrogen, optionally together with any associated dose of progestogen or placebo.

Each dose of the estrogen may be provided in a separate chamber. Similarly, each dose of the progestogen may be provided in a separate chamber. Each dose of estrogen of the first series may be provided with its associated dose of progestogen in the same chamber. Alternatively, each dose of estrogen of the first series may be provided with its associated dose of progestogen in different chambers. In certain embodiments, the second region or regions are free of doses of progestogen.

In some embodiments, each dose of the placebo is provided in a separate chamber. Each dose of estrogen of the second series may be provided with its associated dose of placebo in the same chamber. Alternatively, each dose of estrogen of the second series may be provided with its associated dose of placebo in different chambers. In some embodiments, the first region or regions are free of doses of placebo.

In certain embodiments, the chambers are provided on a roll, a sheet, concentric rings, strips, or another pre-formed interconnection.

The doses may be adapted for oral administration. In certain embodiments, the doses of estrogen, progestogen, or placebo are provided in a tablet, pill, capsule, or gelcap.

Each dose of progestogen may be provided in a tablet, pill, capsule, or gelcap, wherein the tablet, pill, capsule, or gelcap contains the dose of estrogen with which the dose of progestogen is associated. For example, each tablet, pill, capsule, or gelcap may comprise a first compartment and a second compartment, wherein the first compartment contains one dose of progestogen and the second compartment contains the dose of estrogen with which the dose of progestogen is associated. Alternatively, each dose of progestogen may be provided in a tablet, pill, capsule, or gelcap, wherein the tablet, pill, capsule, or gelcap does not contain the dose of estrogen with which the dose of progestogen is associated.

Kit Comprising an Estrogen and a Progestogen

In certain aspects, the invention relates to a kit for providing estrogen and a progestogen as disclosed herein, such as a kit having one container holding doses of estrogen and a second container holding doses of a progestogen, together with instructions for administering them in accordance with an administration cycle as disclosed herein. For example, the kit may comprise a container comprising 84 doses of an estrogen, a container comprising 14 doses of a progestogen, and instructions for ingesting the doses of estrogen and progestogen, wherein the instructions direct a subject to ingest one dose of estrogen and one dose of progestogen daily for 14 consecutive days, and after 14 consecutive days, the instructions direct the subject to ingest one dose of estrogen daily for 70 consecutive days.

Methods of Using Products Comprising an Estrogen and a Progestogen

In certain aspects, the invention relates to a method of using a packaged pharmaceutical product, comprising ingesting one dose of an estrogen and one dose of a progestogen daily from a first region of the product, and when the doses in the first region are exhausted, ingesting one dose of estrogen daily from a second region of the product. In some embodiments, when the doses in the first region are exhausted, the method comprises ingesting one dose of the placebo daily from the second region of the product with each dose of the estrogen from the second series with which the dose of the placebo is associated.

The dose of estrogen may comprise a dose equal or equivalent to about 200 μg to about 8 mg of estriol, such as a dose equal or equivalent to about 400 μg to about 14 mg of estriol. For example, a dose of the estrogen may comprise a dose equal or equivalent to about 200 μg, 300 μg, 400 μg, 500 μg, 600 μg, 700 μg, 800 μg, 900 μg, 1 mg, 2 mg, 3 mg, 4 mg, 5 mg, 6 mg, 7 mg, or 8 mg. In preferred embodiments, a dose of the estrogen comprises a dose equal or equivalent to about 800 μg to about 10 mg of estriol. In more preferred embodiments, a dose of the estrogen comprises a dose equal or equivalent to about 2 mg, 3 mg, 4 mg, 5 mg, 6 mg, 7 mg, or 8 mg of estriol. In some embodiments, a dose of the estrogen comprises 8 mg of estriol.

Ingesting one dose of an estrogen and one dose of a progestogen daily from a first region of the product may comprise ingesting one dose of an estrogen and one dose of a progestogen daily for 5-21 consecutive days. For example, ingesting one dose of an estrogen and one dose of a progestogen daily from a first region of the product may comprise ingesting one dose of an estrogen and one dose of a progestogen daily for 5, 6, 7, 8, 9, 10, 11, 12, 13, 14, 15, 16, 17, 18, 19, 20, or 21 consecutive days, preferably 14 days.

In some embodiments, ingesting one dose of the estrogen daily from a second region of the product comprises ingesting one dose of an estrogen daily for 7-90 days. For example, ingesting one dose of an estrogen daily from a second region of the product may comprise ingesting one dose of an estrogen daily for 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 consecutive days, preferably 70 days.

In some embodiments, ingesting one dose of the placebo daily from a second region of the product comprises ingesting one dose of the placebo daily for 7-90 days, preferably 70 days.

In certain embodiments, successive doses of the estrogen in each series are ingested on successive days of an administration cycle. Each dose of estrogen may be ingested on the day that an administration cycle designates for that dose to be ingested. The product may designate each dose of estrogen with a number, and successive doses of estrogen may be ingested on days that correspond to consecutive numbers.

In some embodiments, the product designates each dose of estrogen with a day of the week or month, and successive doses of estrogen are ingested on days that correspond to successive days of the week or month.

In certain embodiments, the product comprises a blister pack, blister card, or push-through-pack that contains the doses of the estrogen, progestogen, or placebo, and in such embodiments, the method preferably comprises removing one dose of the estrogen, progestogen, or placebo from the blister pack, blister card, or push-through-pack prior to ingesting the dose.

In some embodiments, the product comprises rupturable chambers that contain the doses of the estrogen, progestogen, or placebo, and the method comprises rupturing the chamber containing a dose of the estrogen, progestogen, or placebo prior to ingesting the dose.

In certain embodiments, ingesting a dose consists of ingesting a unit dose.

In preferred embodiments, the method is performed by a woman, such as a post-menopausal woman.

In certain embodiments, ingesting each dose of the estrogen comprises ingestion each dose of the estrogen at about the same time every day. The first dose of estrogen and the first dose of progestogen from the first region may be ingested on a Sunday. Similarly, the first dose of estrogen from the second region may be ingested on a Sunday.

In some embodiments, if one dose is skipped on one day, then two doses are ingested on the following day. Similarly, if two doses are skipped on two consecutive days, then two doses may be ingested on each of the following two days.

Having now described the present invention in detail, the same will be more clearly understood by reference to the following examples, which are included herewith for purposes of illustration only and are not intended to limit the invention.

EXAMPLES

Example 1—Estriol Benefits Cognition in Ovariectomized Mice

Electrophysiology to assess excitatory synaptic transmission is an accepted biomarker for cognitive function in mice, which specifically tests long term potentiation (LTP) during stimulation of the region of the brain responsible for memory, the CA1 region of the hippocampus. Hippocampal electrophysiology was examined in slices from sham surgical mice treated with placebo (SP), ovariectomized mice treated with placebo (OP), and ovariectomized mice treated with estriol (OE). Following high-frequency stimulation of Schaffer collateral fibers to induce LTP in the CA1, stable LTP was observed in slices from SP mice (FIG. 1). LTP was reduced in OP mice as compared to SP mice, consistent with the known deleterious effects upon loss of peripheral estrogen on neurotransmission (FIG. 1). In contrast, OE mice treated with estriol for 9 weeks showed lasting LTP, which was significantly improved over OP mice (FIG. 1). These results are consistent with the known deleterious effects of removing endogenous ovarian hormones on cognitive function. Further, they show that estriol treatment can improve this biomarker for cognitive function.

Figure 4:
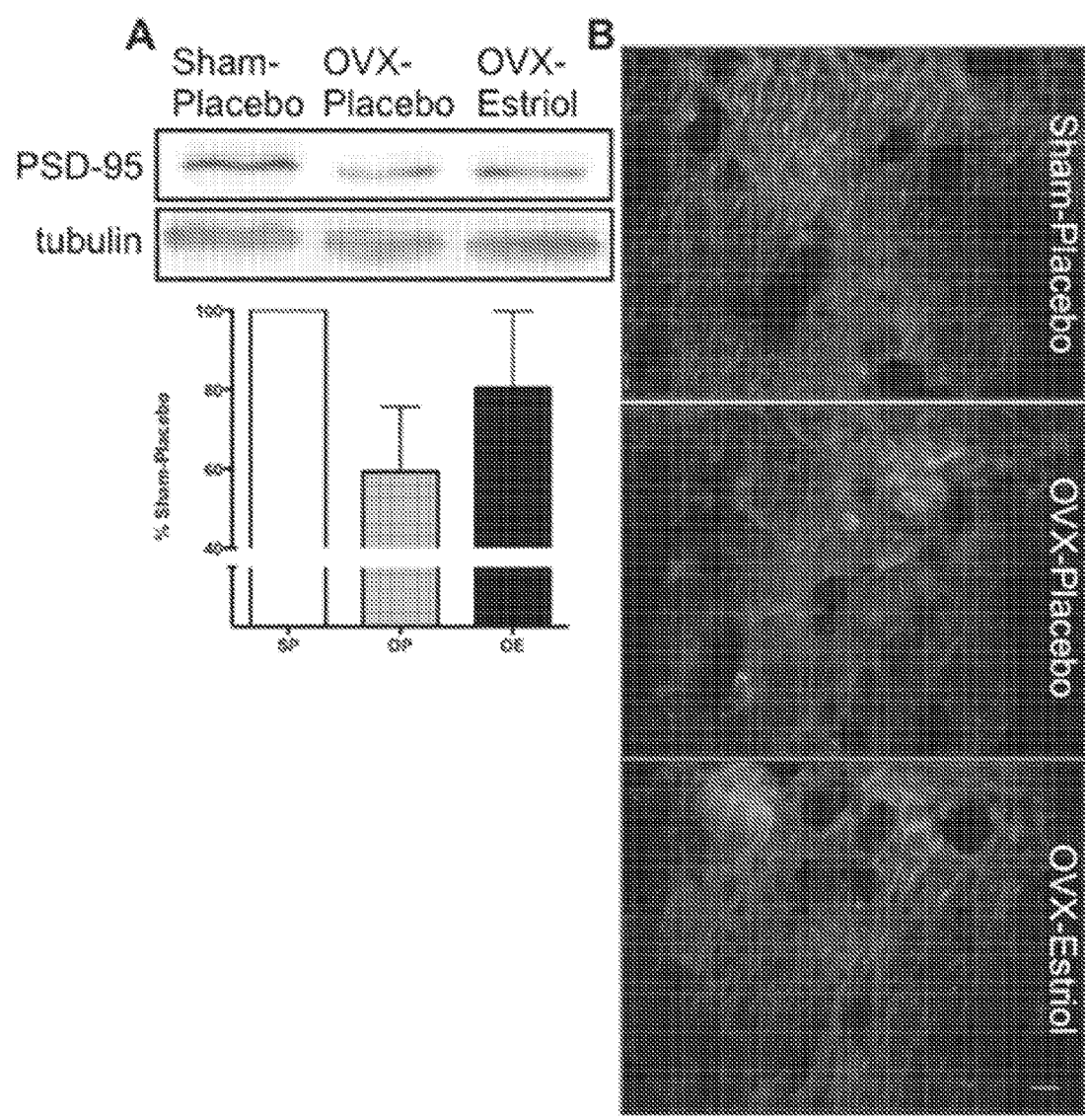
FIG. 4 consists of two panels, labeled panels (A) and (B). Estriol partially recovers synaptic levels of PSD-95 in the dorsal hippocampus following OVX. Panel A: levels of PSD-95 are decreased in the dorsal hippocampus in OVX-Placebo mice (n=2) compared to Sham-Placebo mice (n=2). OVX-Estriol mice show elevated PSD-95 levels (n=2). Panel B: immunofluorescence shows PSD-95 staining in the CA1 stratum radiatum from Sham-Placebo, OVX-Placebo, and OVX-Estriol mice. Scale bar=20 µm, 40× objective.

Additionally, PSD-95 synaptic protein expression was reduced in the hippocampus of OP mice compared to SP mice, thereby revealing the structural change underlying the loss of function by electrophysiology. In contrast, when ovariectomized mice were treated with estriol, (OE mice), there was increased expression of PSD-95, thereby revealing enhanced structural synaptic integrity that coincided with improvement by electrophysiology (FIG. 4). Expression of PSD-95 in the CA1 stratum radiatum was shown by both immunofluorescence and by western blot (FIG. 4)

Taken together, these results demonstrate for the first time that estriol treatment can benefit cognition in the preclinical model of cognitive decline due to loss of ovarian hormones.

Example 2—Estriol-Mediated Cognitive Improvement is Mediated by Estrogen Receptor β

Figure 5:
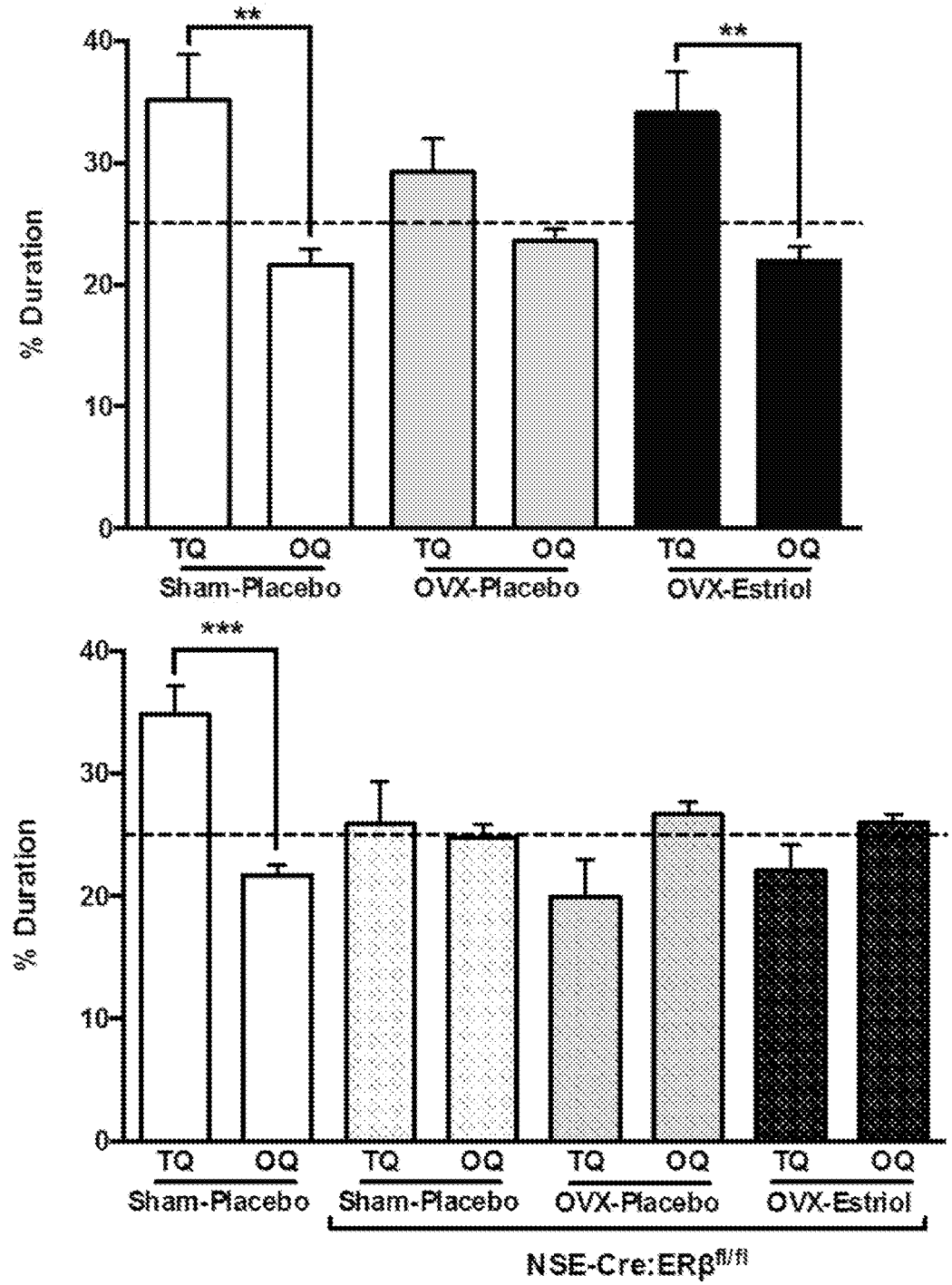
FIG. 5. Peripheral estrogens improve performance on the Morris water maze via ERP expressed on neurons. Healthy female C57BL/6 were tested for cognitive performance (spatial memory) using the Morris water maze, whereby mice learn to spend more time in a target quadrant (TQ) as compared to three other quadrants (OQ). (Top graph) Sham-Placebo mice (SP, n=6) spent more time in the target quadrant due to proper learning, whereas ovariectomized, placebo-treated mice (OVX-Placebo, OP, n=7) did not show learning, thereby confirming that the loss of endogenous ovarian hormones causes cognitive disability. In contrast, ovariectomized, estriol-treated mice (OVX-Estriol, OE, n=7) displayed that the ability to learn may be restored with estriol treatment ($p \leq 0.01$, ANOVA-Sidak's posttest). (Bottom graph) To determine (a) whether ER beta is required for proper learning and, more specifically, (b) whether ER beta expression in neurons is required for learning, mice were generated that had ER beta conditionally knocked out using CreLox technology, with Cre driving the knock out in neurons via the neuron-specific enolase (NSE) promoter. Wild-type SP (n=7), but not SP NSE-Cre: ERβ$^{fl/fl}$ (n=7), OP NSE-Cre:ERβ$^{fl/fl}$ (n=7), or OE NSE-Cre: ERβ$^{fl/fl}$ (n=7) mice, spent significantly greater % duration in the TQ than in the OQ, averaged. (*$p \leq 0.001$, ANOVA-Sidak's posttest). These results suggest that, when ER beta is removed from neurons in the brain, mice lose the ability to learn. Further, these findings suggest that the ability of estriol to rescue learning is mediated by ER beta expression in neurons. The dashed line on the graphs indicates the time expected to be spent in a quadrant by random chance in the absence of learning (25%).
Figure 6:
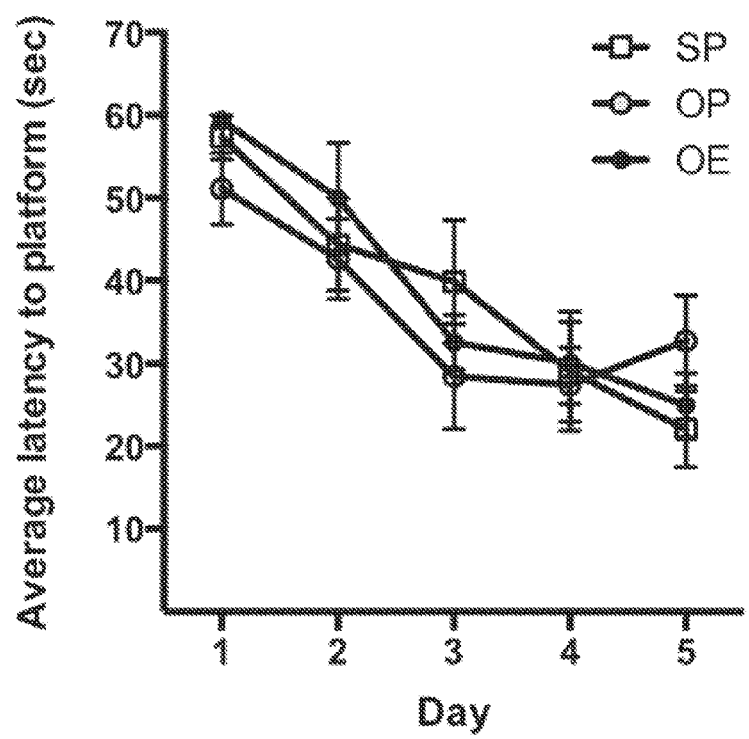
FIG. 6 shows that no difference was observed between Sham-Placebo (SP, n=6), OVX-Placebo (OP, n=7), and OVX-Estriol (OE, n=7) in average latency to platform during acquisition training for the Morris water maze (3 trials/mouse/day, RM-ANOVA p>0.05).

Ovariectomized mice (OVX-Placebo) display worse performance in the Morris water maze than control mice (Sham-Placebo) (FIG. 5, top panel). The administration of an estriol improves performance in ovariectomized mice (OVX-Estriol) (FIG. 5, top panel). Specifically, Sham-Placebo mice (SP) showed a significant preference for the target quadrant (TQ) over other quadrants (OQ), measured by % duration in a target quadrant, while OVX-Placebo mice did not. OVX, estriol-treated (OE) mice (receiving 20 days of 5 mg, 90 day release estriol implants), on the other hand, had a significant preference for the TQ over OQ. No difference was observed between Sham-Placebo (SP, n=6), OVX-Placebo (OP, n=7), and OVX-Estriol (OE, n=7) in average latency to platform during acquisition training (3 trials/mouse/day, RM-ANOVA p>0.05) (FIG. 6), showing that the differences observed in testing between groups was not due to differences in ability to access the platform, but were indeed due to inability to learn and remember.

The effect of estriol on cognition is likely mediated by estrogen receptor β expressed by neurons because estrogen-mediated improvement is lost in mice comprising a conditional knockout of estrogen receptor β in a neuron-specific enolase-CRE mouse (NSE-Cre:ERβ$^{fl/fl}$; FIG. 5, bottom panel). Thus, estrogen receptor β ligands can likely protect against neuronal defects and disability during neurodegenerative processes. This is consistent with the observation that estriol improved performance since it is a known that estriol is an agonist for various estrogen receptors including estrogen receptor β.

Example 3—Use of Estriol and a Progestogen for the Treatment of Menopause

This example describes a randomized, double-blind, placebo-controlled human clinical trial for the treatment of menopause estriol and norethindrone.

Enrollment Criteria

Eligible patients are female, between the age of 45 and 60 years, have not had a menses in at least 12 months, and have had their last menses in the last 5 years. Women who are taking hormone replacement therapy are excluded from the trial.

Study Conduct and Monitoring Schedule

Patients are randomized to oral estriol (2 mg/day, 4 mg/day, 6 mg/day, or 8 mg/day) or to placebo for a 36-month treatment duration. Gynecologists examine the patients before, during, and after the study. Each patient is examined at three- to six-month intervals during the trial. Patients also undergo mammograms before and after the study. In addition, at baseline, 3 months, 6 months, 12 months, 18 months, 24, months, 30 months, and 36 months, the investigators measure participants' estriol levels, and assess cognitive abilities.

A total of 100 patients receive estriol, and 100 patients receive placebo. Baseline characteristics are similar in both patient groups. Participants' mean age at entry is approximately 52 years. Estriol levels in serum are in early pregnancy range in the estriol-treated group. To ensure breast and uterus safety, every three months the patients take norethindrone 0.7 mg once a day for 14 days. This hormone regimen is found to be safe and well tolerated with regard to serious adverse events, adverse events, general exams, blood chemistries, and hematological studies, as well as for gynecological outcomes.

INCORPORATION BY REFERENCE

All patents, published patent applications, and other publications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

I claim:

1. A method of (a) slowing, halting, or reversing cognitive decline or stabilizing or improving cognitive function; (b) slowing, halting, or reversing memory loss or stabilizing or improving memory; or (c) slowing, halting, reversing, stabilizing, or improving a learning disability in a peri- or post-menopausal female subject, comprising:
    administering to the subject, on a continuous basis throughout two or more consecutive treatment periods, estriol; and
    administering to the subject, for only a portion of each treatment period, a progestogen.

2. The method of claim 1, wherein the progestogen is selected from chlormadinone acetate, cyproterone acetate, desogestrel, dienogest, 5α-dihydroprogesterone, drospirenone, ethinodiol acetate, ethynodiol diacetate, etonogestrel, gestodene, 17-hydroxyprogesterone, levonorgestrel, medroxyprogesterone acetate (17α-hydroxy-6α-methylprogesterone acetate), megestrol, megestrol acetate (17α-acetoxy-6-dehydro-6-methylprogesterone), nestorone, nomegestrol acetate, norethindrone, norethindrone acetate, norethynodrel, norgestimate, norgestrel, progesterone, tanaproget, trimegestone, pharmaceutically acceptable salts of any of the foregoing, and any combination thereof.

3. The method of claim 1, wherein each treatment period is at least 28 consecutive days, at least 56 consecutive days, 84 consecutive days, 112 consecutive days, at least 4 consecutive weeks, 8 consecutive weeks, at least 12 consecutive weeks, at least 16 consecutive weeks, at least one month, at least two consecutive months or at least four consecutive months.

4. The method of claim 1, wherein the estriol is administered orally in a dose equal or equivalent to about 200 μg to about 20 mg of estriol daily, about 500 μg to about 8 mg of estriol daily, or about 2 mg of estriol daily.

5. The method of claim 1, wherein the progestogen is administered orally in a dose equal or equivalent to about 70 μg to about 7 mg of norethindrone daily, about 100 μg to about 1 mg of norethindrone daily, or about 700 μg of norethindrone daily.

6. The method of claim 1, wherein the subject is estrogen deficient and the subject has not had estrogen replacement therapy during the period of time in which the subject has been estrogen deficient.

7. A method of (a) slowing, halting, or reversing cognitive decline or stabilizing or improving cognitive function; (b) slowing, halting, or reversing memory loss or stabilizing or improving memory; or (c) slowing, halting, reversing, stabilizing, or improving a learning disability in a peri- or post-menopausal female subject, comprising:
    administering orally to a female subject in need thereof, on a continuous basis for 28 consecutive days (4 weeks), about 4 mg of estriol daily or about 8 mg of estriol daily; and
    administering orally to the subject, for 10 consecutive days of the 28 consecutive days (4 weeks), 0.7 mg of norethindrone daily.

8. The method of claim 7, wherein the 10 consecutive days are the first 10 consecutive days of the 28 consecutive days (4 weeks).

9. A method of (a) slowing, halting, or reversing cognitive decline or stabilizing or improving cognitive function; (b) slowing, halting, or reversing memory loss or stabilizing or improving memory; or (c) slowing, halting, reversing, stabilizing, or improving a learning disability in a peri- or post-menopausal female subject, comprising identifying a peri- or post-menopausal female subject and initiating treatment of the subject by a method as defined in claim 1.

10. The method of claim 1, further comprising testing the cognitive ability of the subject at least two times and comparing the results of at least two tests, wherein the cognitive ability, memory, and/or learning ability of the subject are tested prior to administering the estriol, and the cognitive ability, memory, and/or learning ability of the subject are tested at least once after administering the estriol.

11. The method of claim 10, further comprising increasing the dose of the estriol only if the subject displays cognitive decline, memory loss, and/or learning disability.

12. The method of claim 11, wherein the dose of estriol is increased to a dose equal or equivalent to about 4 to 8 mg of estriol daily administered orally.

13. A packaged pharmaceutical product, comprising:
    a first region comprising a first series of doses of estriol, wherein each dose of the estriol is associated with a dose of a progestogen; and
    a second region comprising a second series of doses of estriol that are not associated with doses of the progestogen,
    wherein each dose of estriol comprises a dose equal or equivalent to about 200 μg to about 8 mg of estriol.

14. The packaged pharmaceutical product of claim 13, wherein a dose of the estriol comprises a dose equal or equivalent to about 400 μg to about 4 mg of estriol, about 800 mg to about 3 mg of estriol, or about 2 mg of estriol.

15. The packaged pharmaceutical product of claim 13, wherein the progestogen is progesterone, 17-hydroxyprogesterone, 5α-dihydroprogesterone, norethindrone, norethindrone acetate, desogestrel, levonorgestrel, medroxyprogesterone acetate, megestrol, chlormadinone acetate, cyproterone acetate, norethynodrel, ethynodiol diacetate, norgestrel, gestodene, norgestimate, dienogest, drospirenone, etonogestrel, nestorone, nomegestrol acetate, trimegestone, tanaproget, or a pharmaceutically acceptable salt of any of the foregoing, or any combination thereof.

16. The packaged pharmaceutical product of claim 13, wherein a dose of the progestogen comprises a dose equal or equivalent to about 70 µg to 7 mg of norethindrone, about 100 µg to 1 mg of norethindrone, or about 700 µg of norethindrone.

17. The packaged pharmaceutical product of claim 13, wherein successive doses of the estriol in each series are associated with successive days of an administration cycle, and the administration cycle consists of 28-365 consecutive calendar days.

18. The method of claim 1, wherein the portion of the treatment period is 10 consecutive days.

19. The method of claim 4, wherein the estriol is administered orally in a dose equal or equivalent to about 4 mg of estriol daily.

20. The method of claim 4, wherein the estriol is administered orally in a dose equal or equivalent to about 8 mg of estriol daily.

* * * * *